(12) United States Patent
Harrer et al.

(10) Patent No.: US 11,219,405 B2
(45) Date of Patent: Jan. 11, 2022

(54) EPILEPSY SEIZURE DETECTION AND PREDICTION USING TECHNIQUES SUCH AS DEEP LEARNING METHODS

(71) Applicant: International Business Machines Corporation, Armonk, NY (US)

(72) Inventors: Stefan Harrer, Hampton (AU); Filiz Isabell Kiral-Kornek, Melbourne (AU); Benjamin Scott Mashford, Parkdale (AU); Subhrajit Roy, Melbourne (AU); Jianbin Tang, Doncaster East (AU)

(73) Assignee: International Business Machines COrporation, Armonk, NY (US)

( * ) Notice: Subject to any disclaimer, the term of this patent is extended or adjusted under 35 U.S.C. 154(b) by 157 days.

(21) Appl. No.: 15/968,283

(22) Filed: May 1, 2018

(65) Prior Publication Data
US 2019/0336061 A1 Nov. 7, 2019

(51) Int. Cl.
*A61B 5/00* (2006.01)
*G16H 50/20* (2018.01)
(Continued)

(52) U.S. Cl.
CPC ........ *A61B 5/4094* (2013.01); *A61B 5/02055* (2013.01); *A61B 5/681* (2013.01);
(Continued)

(58) Field of Classification Search
CPC ... A61B 5/4094; A61B 5/7275; A61B 5/7282; A61B 5/7264; A61B 2562/0219;
(Continued)

(56) References Cited

U.S. PATENT DOCUMENTS 5,816,247 A * 10/1998 Maynard .................. A61B 5/04
128/731
5,999,846 A * 12/1999 Pardey ..................... A61B 5/04
600/544
(Continued)

FOREIGN PATENT DOCUMENTS

CN   104225790 A   12/2014
CN   107049239 A    8/2017
(Continued)

OTHER PUBLICATIONS

He; Tianxing, Reshaping Deep Neural Network for Fast Decoding By Node-Pruning, May 2014, IEEE, 2014 IEEE International Conference on Acoustics, Speech, and Signal Processing (ICASSP), p. 246 (Year: 2014).*
(Continued)

*Primary Examiner* — Amanda K Hulbert
(74) *Attorney, Agent, or Firm* — Harrington & Smith

(57) ABSTRACT

One or both of epilepsy seizure detection and prediction at least by performing the following: running multiple input signals from sensors for epilepsy seizure detection through multiple classification models, and applying weights to outputs of each of the classification models to create a final classification output. The weights are adjusted to tune relative output contribution from each classifier model in order that accuracy of the final classification output is improved, while power consumption of all the classification models is reduced. One or both of epilepsy seizure detection and prediction are performed with the adjusted weights. Another method uses streams from sensors for epilepsy seizure detection to train and create the classification models, with fixed weights once trained. Information defining the classification models with fixed weights is communicated to wearable computer platforms for epilepsy seizure detection
(Continued)

and prediction. The streams may be from multiple people and applied to an individual person.

20 Claims, 10 Drawing Sheets

(51) Int. Cl.
| | | |
|---|---|---|
| *A61B 5/0205* | (2006.01) | |
| *A61B 5/01* | (2006.01) | |
| *A61B 5/318* | (2021.01) | |
| *A61B 5/369* | (2021.01) | |
| *A61B 5/389* | (2021.01) | |

(52) U.S. Cl.
CPC .......... *A61B 5/7267* (2013.01); *A61B 5/7275* (2013.01); *G16H 50/20* (2018.01); *A61B 5/01* (2013.01); *A61B 5/318* (2021.01); *A61B 5/369* (2021.01); *A61B 5/389* (2021.01); *A61B 2562/0219* (2013.01)

(58) Field of Classification Search
CPC ....... A61B 5/01; A61B 5/02055; A61B 5/318; A61B 5/369; A61B 5/389; A61B 5/681; A61B 5/7267; G61H 50/20; G16H 10/60; G16H 20/70; G16H 50/20
USPC .................................. 600/300, 301, 544, 545
See application file for complete search history.

(56) References Cited

U.S. PATENT DOCUMENTS

| | | | | |
|---|---|---|---|---|
| 6,678,548 | B1* | 1/2004 | Echauz | A61B 5/04 |
| | | | | 600/544 |
| 7,720,683 | B1* | 5/2010 | Vermeulen | G10L 15/04 |
| | | | | 704/254 |
| 9,332,939 | B2 | 5/2016 | Osorio | |
| 2004/0181162 | A1 | 9/2004 | Wilson | |
| 2006/0111644 | A1 | 5/2006 | Guttag et al. | |
| 2012/0101401 | A1 | 4/2012 | Faul et al. | |
| 2013/0231580 | A1 | 9/2013 | Chen et al. | |
| 2014/0358025 | A1 | 12/2014 | Parhi et al. | |
| 2016/0022162 | A1 | 1/2016 | Ong et al. | |
| 2016/0183828 | A1 | 6/2016 | Ouyang et al. | |
| 2017/0258410 | A1 | 9/2017 | Gras | |
| 2018/0032867 | A1* | 2/2018 | Son | G06N 3/08 |
| | | | | 706/25 |
| 2018/0289310 | A1* | 10/2018 | Girouard | A61B 5/4094 |

FOREIGN PATENT DOCUMENTS

| | | |
|---|---|---|
| CN | 107679564 A | 2/2018 |
| WO | 2017120166 A1 | 7/2017 |

OTHER PUBLICATIONS

E. Juarez-Guerra, V. Alarcon-Aquino, P. Gomez-Gil "Epilepsy Seizure Detection in EEG Signals Using Wavelet Transforms and Neural Networks" In Lecture Notes in Electrical Engineering, 261-269. Springer Verlag, (Jan. 1, 2015).
Sriram Ramgopal et al. "Seizure Detection, Seizure Prediction, and Closed-Loop Warning Systems in Epilepsy" Epilepsy & Behavior 37, pp. 291-307 (Apr. 17, 2014).
Wen Zhu et al. "Sensitivity, Specificity, Accuracy, Associated Confidence Interval and ROC Analysis with Practical SAS Implementations", Northeast SAS User Group Proceedings, Section of Health Care and Life Sciences, Baltimore, Maryland, Nov. 14-17, 2010 pp. 1-9.
"How Neural Networks are Trained" https://ml4a.github.io/ml4a/how_neural_networks_are_trained/ [retrieved Mar. 27, 2018].
International Search Report, PCT/IB2019/052533, dated Aug. 20, 2019, 9 pages.

* cited by examiner

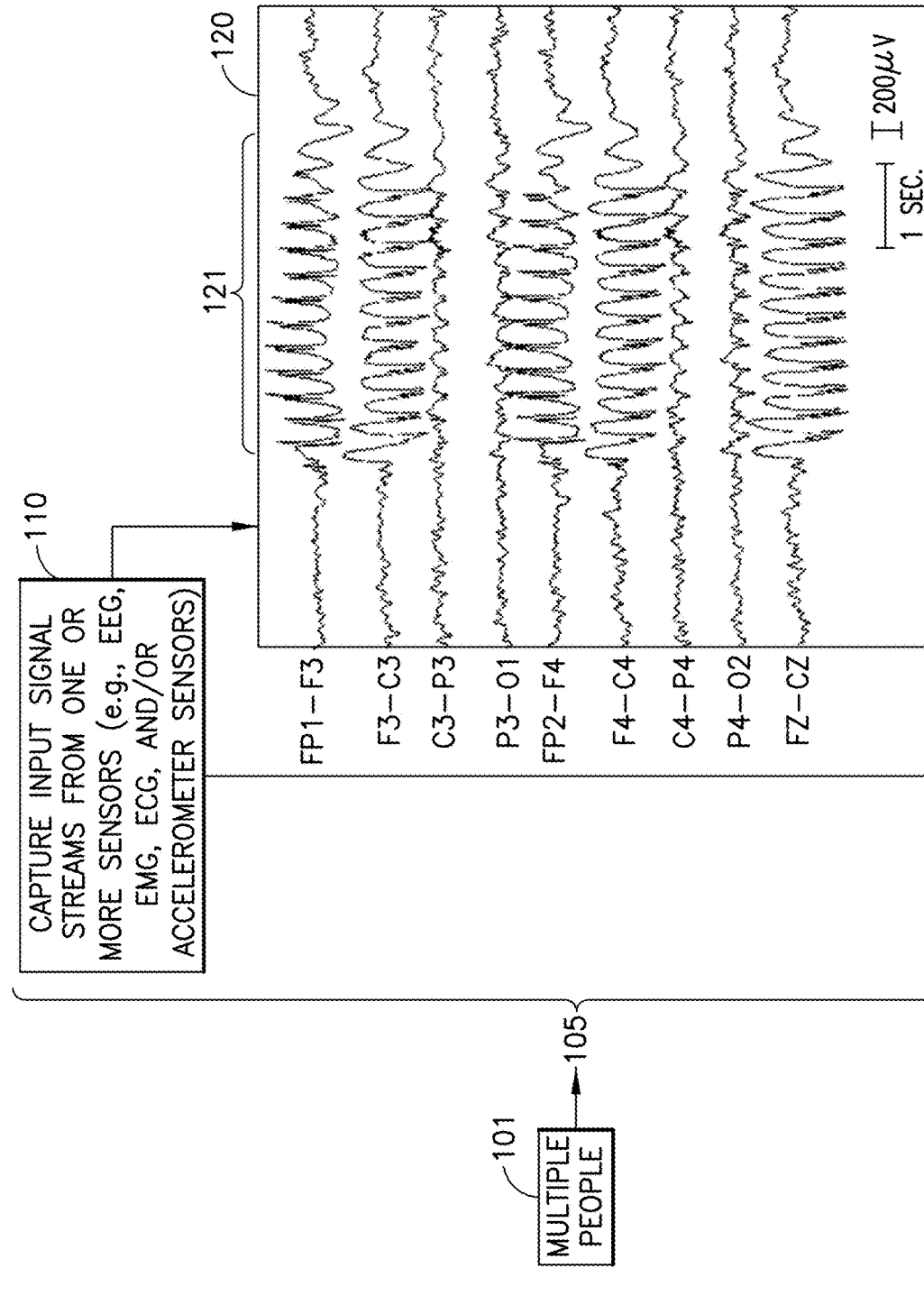

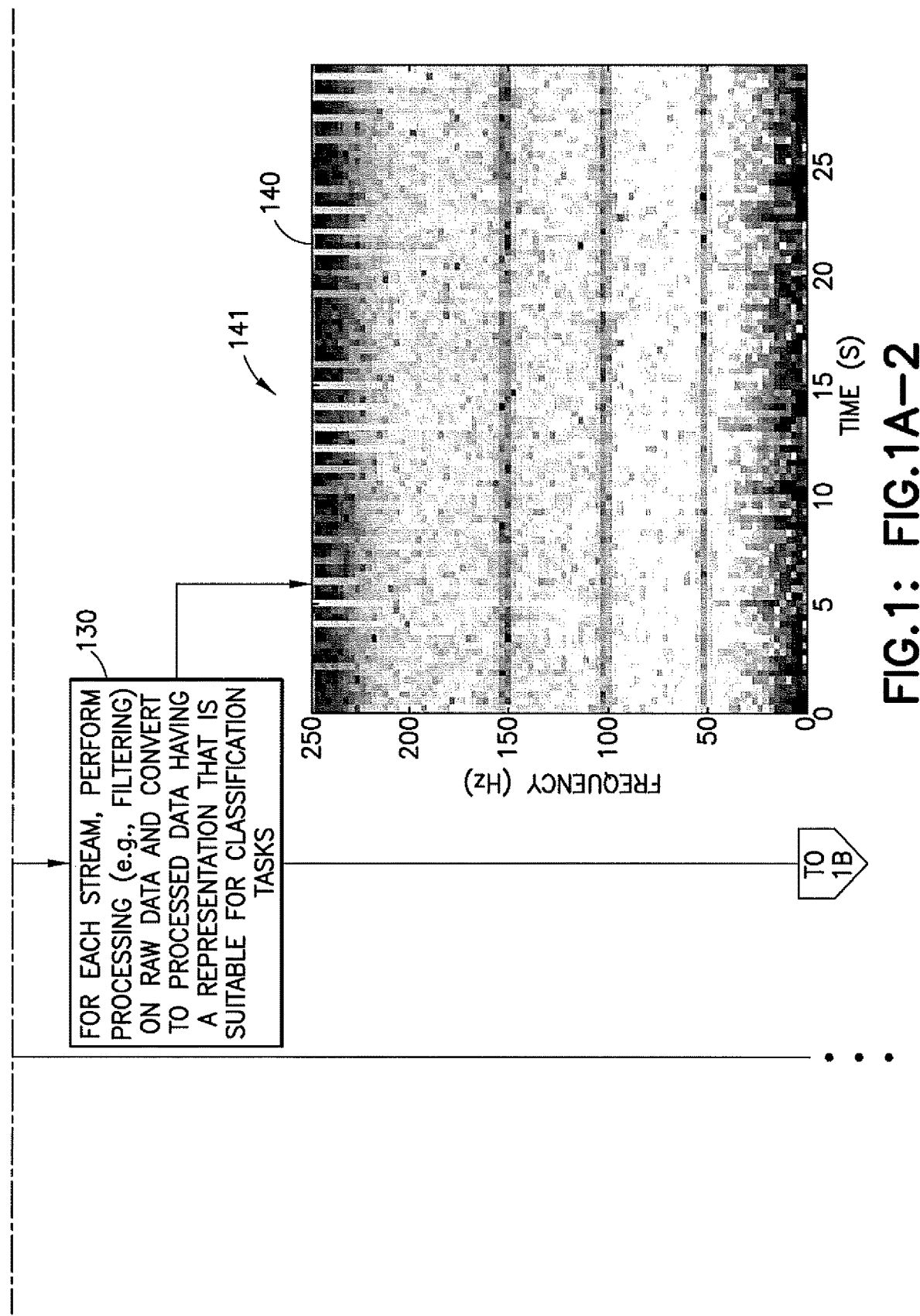
FIG.1: FIG.1A-2

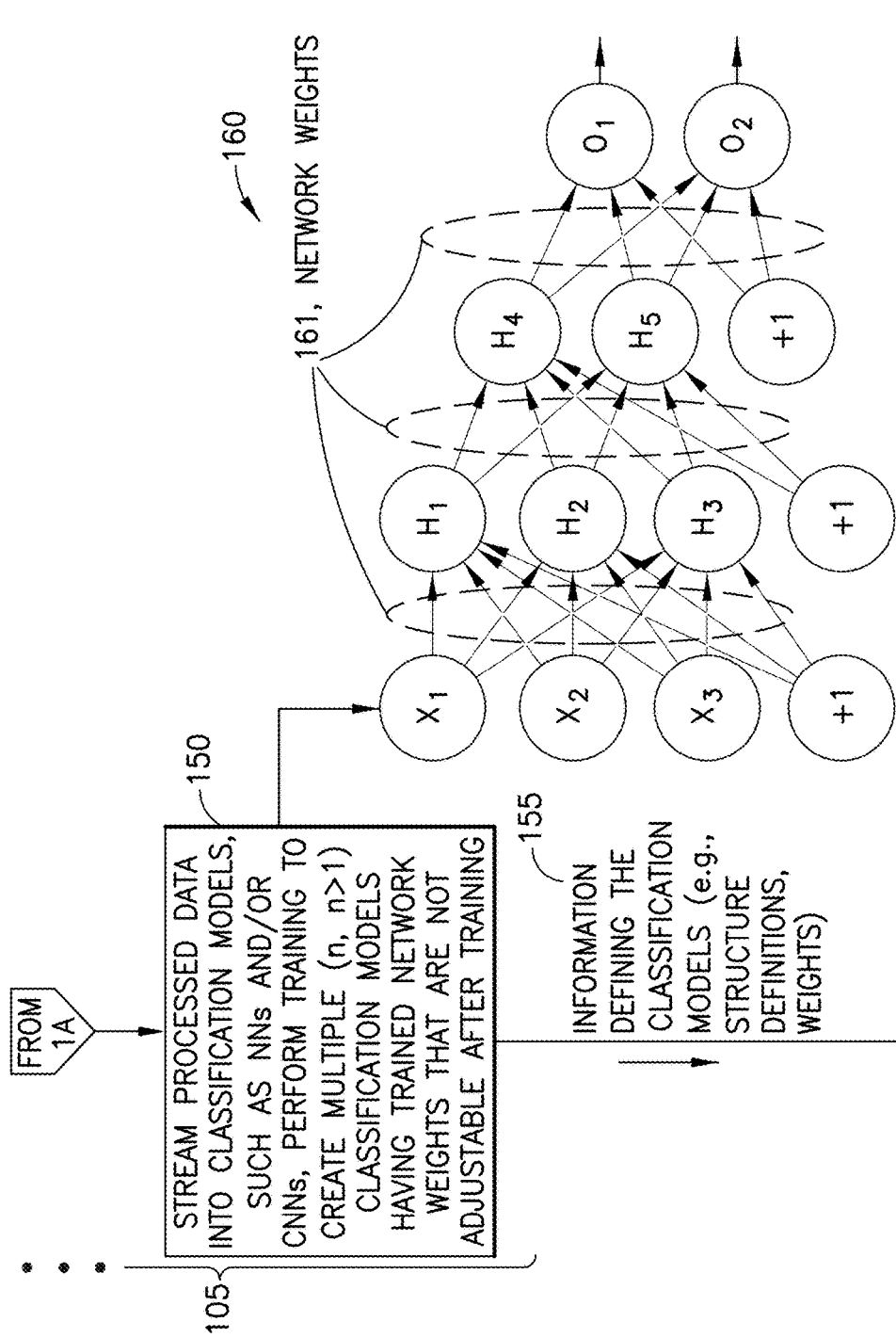

EPILEPSY SEIZURE DETECTION AND PREDICTION USING TECHNIQUES SUCH AS DEEP LEARNING METHODS

BACKGROUND

This invention relates generally to detection of seizures and, more specifically, relates to epilepsy seizure detection and prediction using techniques such as deep learning methods.

This section is intended to provide a background or context to the invention disclosed below. The description herein may include concepts that could be pursued, but are not necessarily ones that have been previously conceived, implemented or described. Therefore, unless otherwise explicitly indicated herein, what is described in this section is not prior art to the description in this application and is not admitted to be prior art by inclusion in this section. Abbreviations that may be found in the specification and/or the drawing figures are defined below, after the main part of the detailed description section.

Epilepsy is a neurological disorder marked by sudden recurrent episodes of sensory disturbance, loss of consciousness, or convulsions. These are commonly referred to as seizures. Although the symptoms of a seizure may affect any part of the body, the electrical events that produce the symptoms occur in the brain. The location of that event, how it spreads, how much of the brain is affected, and how long it lasts all have profound effects. These factors determine the character of a seizure and its impact on the individual.

Epilepsy is a disease that is characterized by a diverse range of neurological activity signals. These signals can be analyzed using sensors such as electroencephalography (EEG) sensors. More specifically, electroencephalograms (EEGs) have been employed to record electrical signals as waveforms generated by different parts of the brain. These EEGs can be analyzed and can be used to determine if a person is having a seizure or even predict an oncoming seizure.

Initially, EEGs were only performed and their waveforms analyzed by trained personnel, mainly doctors. Since computing performance and prediction techniques have improved dramatically, computers have been used to perform and analyze these waveforms. For instance, neural networks and particularly convolutional neural networks (CNNs) have been applied to this field, and the models based on CNNs have proved successful in analysis and prediction of epileptic seizures. Furthermore, improvement in miniaturization of electronic devices and reduction in power of those devices even while computing performance is maintained or improved has led to the use of mobile computing platforms that are able to perform these analyses. Those mobile computing platforms are now being applied to areas such as analysis and prediction of epileptic seizures and can be miniaturized to the extent the platforms can be wearable or used on other battery-powered devices such as portable platforms used in hospitals. While these provide benefits, they could be improved, particularly for analysis and prediction of epileptic seizures.

SUMMARY

This section is meant to be exemplary and not meant to be limiting.

In an exemplary embodiment, a method is disclosed. The method includes performing one or both of epilepsy seizure detection and prediction at least by performing the following: running a plurality of input signals from sensors for epilepsy seizure detection through a plurality of classification models; and applying weights to outputs of each of the classification models to create a final classification output. The method also includes adjusting the weights to tune relative output contribution from each classifier model in order that accuracy of the final classification output is improved, while power consumption of all the classification models is reduced. The method further includes performing the one or both of epilepsy seizure detection and prediction with the adjusted weights.

In an additional example, an apparatus comprises one or more memories comprising program instructions and one or more processors. The one or more processors cause, in response to retrieval and execution of the program instructions, operations comprising: performing one or both of epilepsy seizure detection and prediction at least by performing the following: running a plurality of input signals from sensors for epilepsy seizure detection through a plurality of classification models; and applying weights to outputs of each of the classification models to create a final classification output; adjusting the weights to tune relative output contribution from each classifier model in order that accuracy of the final classification output is improved, while power consumption of all the classification models is reduced; and performing the one or both of epilepsy seizure detection and prediction with the adjusted weights.

In a further exemplary embodiment, another method is disclosed that includes accessing input signal streams from multiple sensors for epilepsy seizure detection, and performing processing on the input signal streams to convert to processed data having one or more representations suitable for classification tasks. The method also includes streaming processed input signal streams into a plurality of classification models for one or both of epilepsy seizure detection and prediction and performing training to create multiple classification models having trained network weights that are not adjustable after training. The method further includes sending information defining the plurality of classification models with their trained network weights that are not adjustable to one or more wearable computer platforms for use by the one or more wearable computer platforms to perform one or both of epilepsy seizure detection and prediction.

BRIEF DESCRIPTION OF THE SEVERAL VIEWS OF THE DRAWINGS

FIG. 4A-1 and FIG. 4A-2, is a block diagram use of a weighted ensemble of classifier models for an inline application of epilepsy seizure detection and prediction in accordance with an exemplary embodiment;

DETAILED DESCRIPTION

Figures 1, 1B, 2:
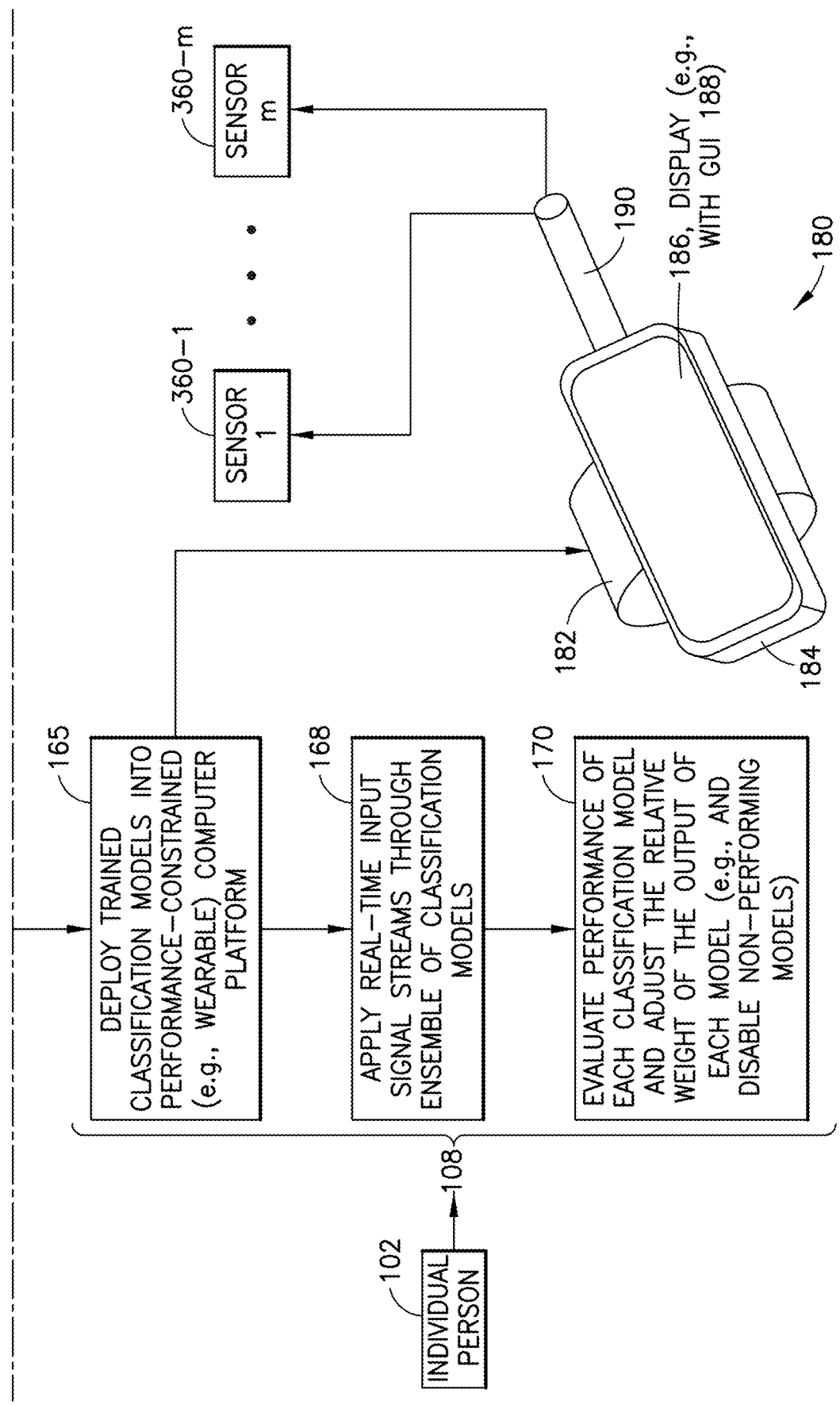
FIG. 1, split over FIG. 1A (itself split over FIGS. 1A-1 and 1A-2) and FIG. 1B (itself split over FIGS. 1B-1 and 1B-2), presents a system overview for a system for epilepsy seizure detection and prediction using techniques such as deep learning methods in accordance with an exemplary embodiment.
FIG. 2 is a block diagram of learning computer platform used for an offline training phase for epilepsy seizure detection and prediction using techniques such as deep learning methods, in accordance with an exemplary embodiment.
Figure 2:
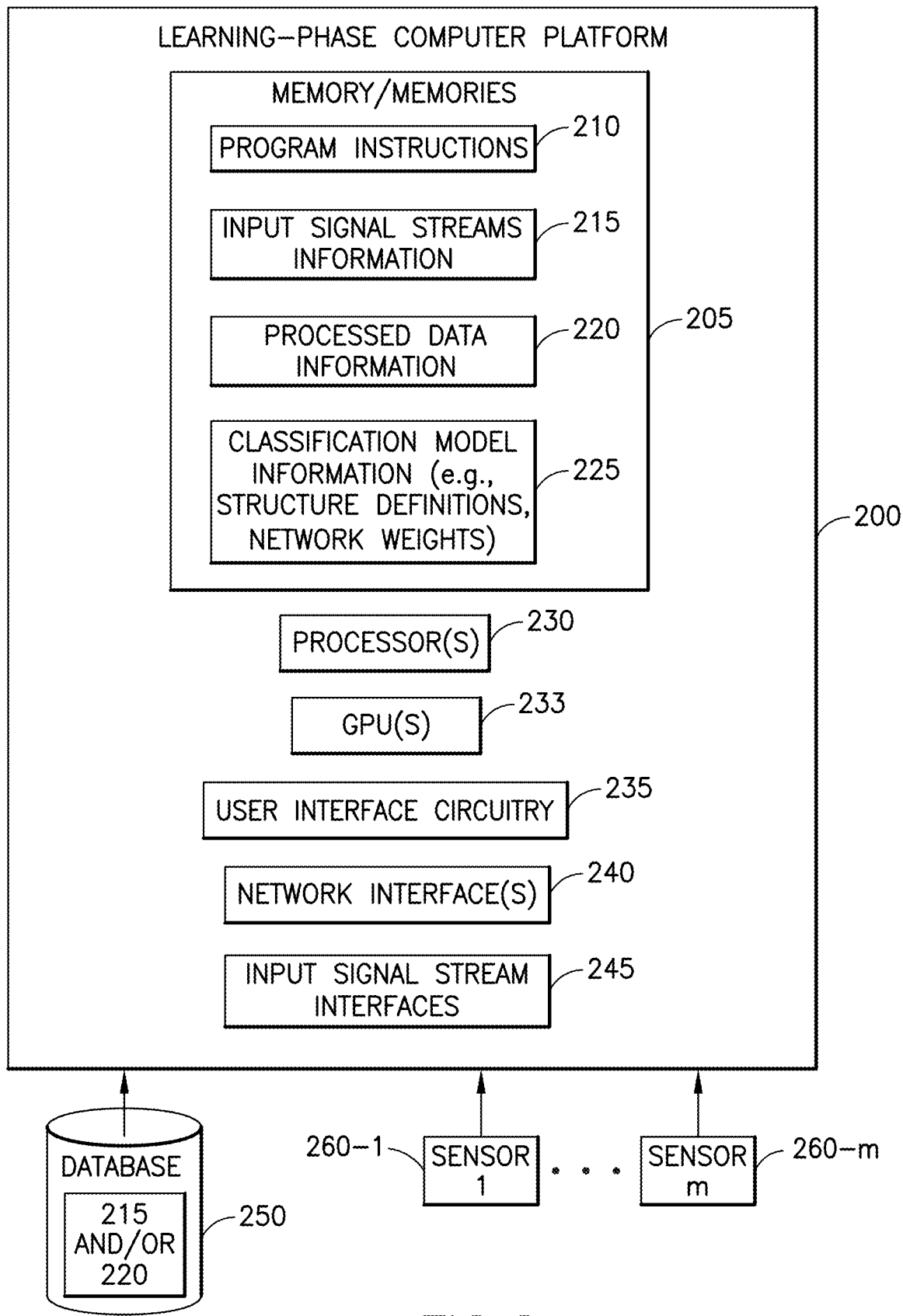

As stated above, mobile computing platforms are now being applied to areas such as analysis and prediction of epileptic seizures. Analyses tools for analysis and prediction of epileptic seizures include neural networks (NNs) such as convolutional neural networks (CNNS). CNNs are very effective at finding patterns in these signals and classifying signal events. Training CNNs requires a large amount of data, but epilepsy patients typically do not have seizures very often.

In an exemplary embodiment, we propose to leverage existing training data (e.g., from other patients) to reduce the amount of time required to develop an effective seizure detection and prediction system for an individual patient. This system uses a classifier. Ultimately, the classifier might run on a wearable computer platform. It is assumed, due to performance limitations in computing power and also battery power to enable the computing, such platforms will be capable of inference tasks (i.e., analyzing streaming input data) but might not be capable of training new classifiers. We therefore implement a system that employs an ensemble of pre-trained classifier models, but is able to adapt these to work effectively on a new patient. One exemplary goal is to minimize power consumption on a wearable device by using the smallest CNN model(s) possible while providing a highest classification accuracy. In this example, small CNN models may be gauged (e.g., relative to large models) by amount of computational resources used, but other options are also possible.

As additional overview, an exemplary system combines online and offline training of deep learning classifiers for analyzing brain activity in epilepsy patients to detect and predict seizure events. Deep learning is part of a broader family of machine learning methods based on learning data representations, as opposed to task-specific algorithms. Deep learning architectures may include deep neural networks, deep belief networks, recurrent neural networks, and the like. Performance-constrained computing hardware, constrained via one or both of computing power and battery power, is assumed to be able to perform inference (online, real-time classification of epilepsy signals) but is assumed to not possess enough computing power (and possibly battery power to perform the computing) to train a CNN. The training of a new CNN is therefore performed on higher performance computing hardware, perhaps with a powerful graphics processing unit (GPU), and is performed offline. That is, the offline component is the phase where the weights in the classification model are trained before a fixed-weights model is deployed to the wearable device. The wearable device may contain a TrueNorth platform, from International Business Machines Corporation (IBM). IBM is an American multinational technology company headquartered in Armonk, N.Y., United States. IBM states that TrueNorth is a brain-inspired processor that has a parallel, distributed, modular, scalable, fault-tolerant, flexible architecture that integrates computation, communication, and memory and has no clock.

The online component combines the output of an ensemble of analytical models. These models are all deployed simultaneously to the wearable device and the final prediction is made via trainable output from, e.g., a simple (e.g., perceptron-style) NN (see, e.g., FIG. 4A as an example). The deployed platform in use by a patient may also include a graphical user interface (GUI) (e.g. touchscreen) that enables the patient to provide real-time feedback to the online classifier. Events such as "I had a seizure 5 minutes ago" may be compared with the outputs from the classification models and a weighted output of the models may be updated accordingly. EEG data and/or data from other sensors can further be sent to a clinician for classification/verification, especially early in the treatment, to further train the online classifier (e.g., which uses an ensemble of multiple classification models). Retraining of the offline component may be performed periodically during visits to the doctor/technician, e.g., using stored data from a wearable platform.

One exemplary advantage includes the use of repeated cycles of online and offline training to personalize and optimize performance of a machine learning classifier on a wearable platform. Another exemplary advantage includes, during the online training phase, the parallel use of multiple independent classifier models whose individual outputs are weighted by a single classifier to produce a final classification result. A further exemplary advantage includes, in response to a weighted 'usefulness' of a particular classifier falling below a certain threshold, this classifier is 'switched off' entirely, thereby reducing power consumption on the wearable computing platform.

Additional detail is now provided. Referring to FIG. 1, which is split over FIGS. 1A and 1B, this figure presents a system overview for a system for epilepsy seizure detection and prediction using techniques such as deep learning methods, in accordance with an exemplary embodiment. FIG. 1 depicts an offline training phase 105, described with reference to blocks 110, 130, and 150. The offline training phase 105 is performed by a learning-phase computer platform 200, described below in reference to FIG. 2. The offline training phase 105 may use data from multiple (e.g., many) different people. See reference 101. FIG. 1 further depicts a real-time, online phase 108, described with reference to blocks 165, 168, and 170. The real-time, online phase 108 is performed by a performance-constrained (e.g., wearable) computer platform 300, described below in reference to FIG. 3. The real-time, online phase 108 is applied to a single, individual person. See reference 102. This allows data captured potentially from many people (reference 101) to be used to create "fixed" neural networks, which are then used for a single, individual person (reference 102), who may or may not be (e.g., likely is not) part of the many people from reference 101. The online phase 108 should therefore start with a good baseline set of trained neural networks, which should require much less extensive training to be able to perform epilepsy seizure detection and prediction for the individual using the online phase 108.

The offline training phase 105 starts in block 110, when a learning-phase computer platform 200 captures input signal streams from one or more sensors (e.g., EEG, EMG, ECG, and/or accelerometer sensors). One example in terms of EEG sensors is illustrated by reference 120, which contains EEG traces (in μV) versus time (in seconds, sec.). Each EEG trace corresponds to standard EEG electrode names (and their corresponding positions). That is, the EEG trace for "FP1-F3" is for well-known FP1 (a frontal parietal lobe placement) and F3 (a frontal lobe placement) placements of EEG electrodes on a head. These EEG traces illustrate an epileptic seizure in the region indicated by reference 121.

The learning-phase computer platform 200 in block 130, for each stream, performs processing (e.g., filtering) on raw data and converts the raw data to processed data 141 having a representation that is suitable for classification tasks. One such representation is illustrated by reference 140, which is a 2D representation of processed data 141 in a graph of frequency (in Hertz) versus time (in seconds). Reference 140 only shows a single channel of EEG waveform (mapped into frequency domain). Each recording channel will have a similar 2D representation.

In block 150, the learning-phase computer platform 200 streams processed data 141 into classification models, such as NNs and/or CNNs, to train and create multiple (n, n>1) classification models having trained network weights that are not adjustable after training. Typically, a library of pre-trained classification models will be selected by a human operator. The classification models would be chosen based upon their expected suitability to the particular task at hand. One such model is illustrated by reference 160, which illustrates a structure of a relatively simple NN having three input nodes $x_1$, $x_2$, and $x_3$, five hidden nodes $H_1$, $H_2$, $H_3$, $H_4$, and $H_5$, three bias nodes (with +1 in each), and two output nodes $O_1$ and $O_2$, each of which produces corresponding output. The network weights 161 are weights applied at each arrow between the nodes. This is merely exemplary, but is meant to illustrate a type of NN that might be used. Block 150 trains the classification models, using the streamed processed data, to create the trained multiple (n, n>1) classification models.

The real-time, online phase 108 is described with reference to blocks 165, 168, and 170, and is performed by a performance-constrained computer platform 300 (see FIG. 3, described below). The wearable computer platform 180 shown in FIG. 1B is one example of a performance-constrained computer platform 300.

In block 165, the performance-constrained computer platform 300 deploys trained classification models into a performance-constrained (e.g., wearable) computer platform. Block 165 may be thought of as being part of either or both of phases 105 or 108, as information 155 defining the classification models (e.g., structure definitions, network weights) is sent by the learning-phase computer platform 200 toward the performance-constrained computer platform 300 and is received by the performance-constrained computer platform 300. It is assumed, however, that block 165 includes configuration of the classification models and an initial weighting of the outputs of the models, as described in more detail below. Thus, block 165 is included with the inline phase 108.

In block 168, the performance-constrained computer platform 300 applies real-time input signal streams through an ensemble of classification models. The performance-constrained computer platform 300 in block 170 evaluates performance of each classification model and adjusts the relative weight of the output of each model. As described below, it is also possible to disable non-performing models.

Wearable computer platform 180 is one example of a performance-constrained computer platform 300. The wearable computer platform 180 comprises a wrist band 182, a body 184, and a connection 190 for a wearable sensor pack, which in this example includes m sensors 360-1 through 360-m. Note that the body 184 itself may have sensors in it, such as temperature, accelerometer, or other sensors. These are not shown. The body 184 includes a display 186, typically with a GUI 188 to allow a user to configure the wearable computer platform 180 and to view results of the wearable computer platform 180. The wearable computer platform 180 could also communicate wirelessly with other devices. For instance, if the wearable computer platform 180 is used in a doctor's office or a hospital, the wearable computer platform 180 might communicate with a laptop the doctor is using or hospital equipment, e.g., in an intensive care unit.

Turning to FIG. 2 in addition to FIG. 1, FIG. 2 is a block diagram of learning phase computer platform 200 used for an offline training phase for epilepsy seizure detection and prediction using techniques such as deep learning methods, in accordance with an exemplary embodiment. As described above, the learning-phase computer platform 200 is used in an offline training phase 105. The learning-phase computer platform 200 comprises one or more memories 205, one or more processors 230, one or more GPU(s) 233, user interface circuitry 235, one or more network interfaces 240, and input signal stream interfaces 245. The one or more memories 205 comprise program instructions 210, input signal stream information 215, processed data information 220, and classification model information 225 (e.g., comprising structure definitions and network weights for each model of n classification models). The one or more processors 230 (and possibly the GPU(s) 233, if used) retrieve and execute the program instructions 210, to cause the learning-phase computer platform 200 to perform operations as described herein.

The one or more processors 230 comprise circuitry that causes the learning-phase computer platform 200 to perform operations. The one or more GPU(s) 233 comprise circuitry for performing graphics processing, and this graphics processing can be used to train NNs and CNNs and other models used for epilepsy detection and prediction. Use of GPU(s) 233 is optional but can speed processing.

The user interface circuitry 235 is circuitry that allows a user to interact with the learning-phase computer platform 200, e.g., via one or more user interfaces. These user interfaces are not shown, but could include a display, keyboard, mouse, and the like. The learning-phase computer platform 200 may also be a server and accessed via a network.

The network interface(s) 240 are wired or wireless interfaces allowing, e.g., performance-constrained computer platforms 300 and users to interact with the learning-phase computer platform 200. The input signal string interfaces 245 are interfaces for the m sensors 260-1 through 260-m, and may include such circuitry as analog-to-digital converters and the like.

In one example, blocks 110, 120 and 150 of FIG. 1 are performed using the sensors 260-1 through 260-n, and the learning-phase computer platform 200 creates the input signal stream information 215 (e.g., describing the waveforms in reference 120) from signals from the sensors 260-1 through 260-n, and creates the processed data information 220 (corresponding to, e.g., processed data 141 illustrated by reference 140 of FIG. 1). This is typically performed from multiple, even many, patients, although may be additionally from the patient to use the performance-constrained computer platform 300 (see FIG. 3). The learning-phase computer platform 200 also creates classification model 225 information for n classification models (see classification models 420 of FIG. 4A). This information might comprise structure definitions (e.g., type of model, how many layers and nodes, and the like) and network weights 161 for each structure.

Alternatively or in addition, the learning-phase computer platform 200 may access the database 250, which contains input signal streams information 215 and/or processed data information 220. The input signal streams information 215 and/or processed data information 220 stored in the database 250 has already been gathered using sensors 260 (or similar sensors from other systems). The data in the database 250 may be from multiple, or even many, patients, and/or from the patient to use the performance-constrained computer platform 300 (see FIG. 3). The blocks 110, 130, and 150 are performed by the learning-phase computer platform 200 on this data.

Figure 3:
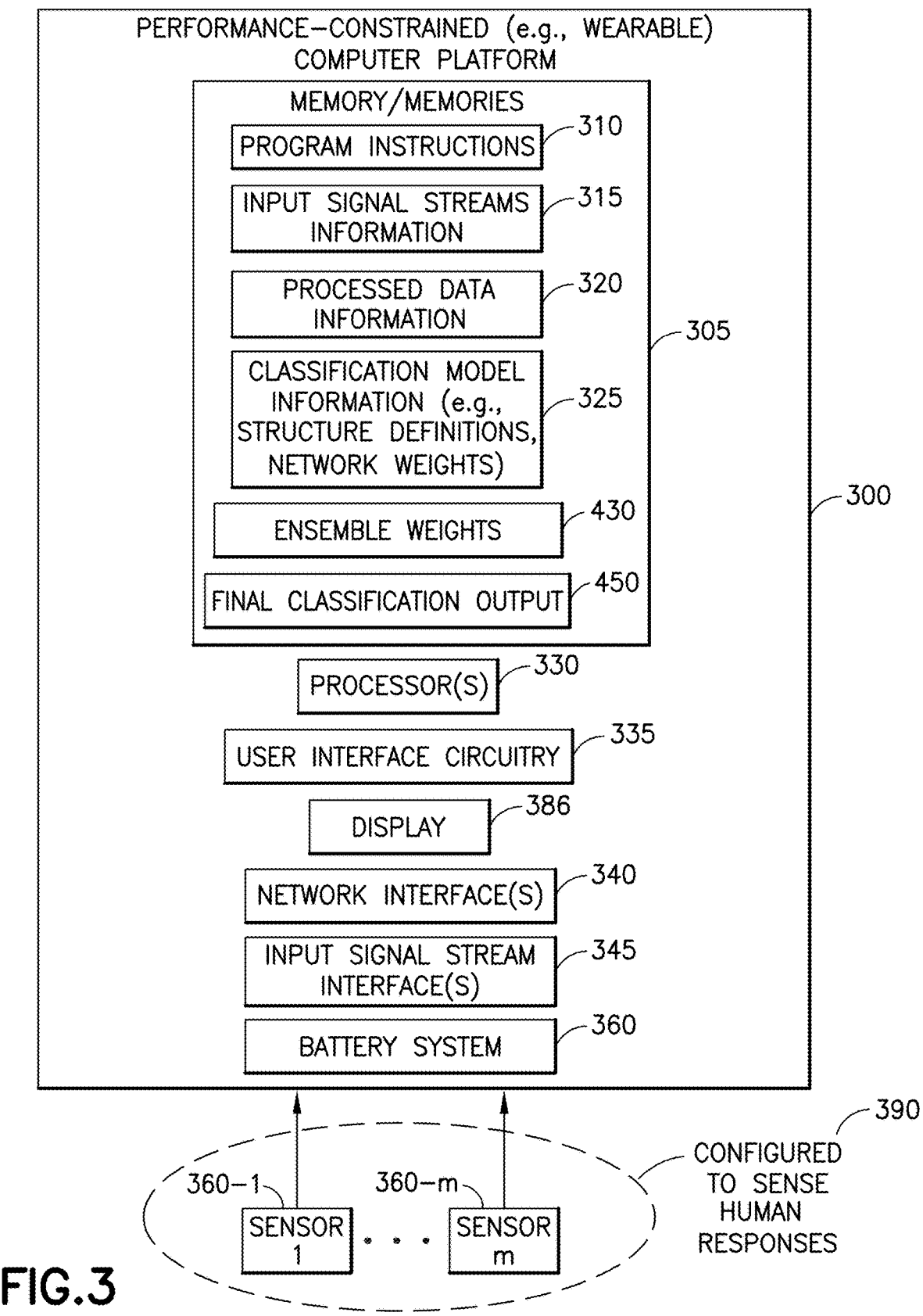
FIG. 3 is a block diagram of a power-constrained (e.g., wearable) computer platform used for real-time, online analysis of epilepsy seizure detection and prediction, in accordance with an exemplary embodiment.

Referring to FIG. 3, this figure is a block diagram of a power-constrained (e.g., wearable) computer platform used for real-time, online analysis of epilepsy seizure detection and prediction, in accordance with an exemplary embodiment. As described above, the performance-constrained computer platform 300 is used in a real-time, online phase 108. The performance-constrained computer platform 300 comprises one or more memories 305, one or more processors 330, user interface circuitry 335, a display 386, one or more network interfaces 340, input stream interfaces 345, and a battery system 360. The one or more memories 305 comprise program instructions 310, input signal streams information 315, processed data information 320, and classification model information 325 (e.g., comprising structure definitions and network weights for each model of n models). The one or more processors 330 are circuity that retrieves and executes the program instructions 310, to cause the performance-constrained computer platform 300 to perform operations as described herein.

The input signal stream information 315 (e.g., describing the waveforms in reference 120) is information from signals from the sensors 360-1 through 360-$n$. As indicated by block 390, the sensors 360 are configured to sense human responses. Typically, for epileptic seizure detection and predication, sensors that may be used include EEG, EMG, ECG, and/or accelerometer sensors. Certain or all of the sensors 360 could be attached to a human being (not shown) in order to create waveforms such as those shown in reference 120 of FIG. 1A. The performance-constrained computer platform 300 creates the processed data information 320 (corresponding to, e.g., processed data 141 illustrated by reference 140 of FIG. 1).

Figures 1, 4A:
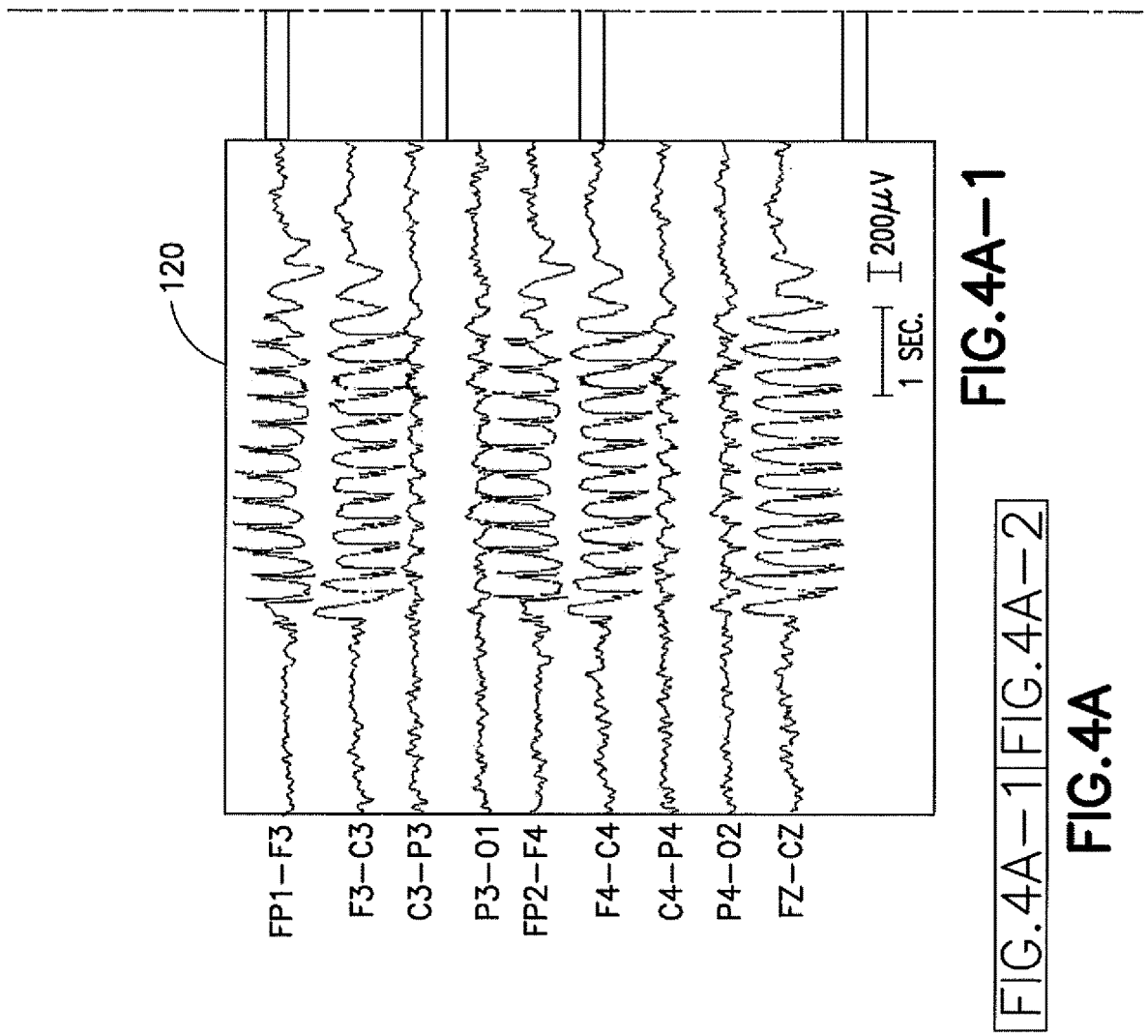
FIG. 4A, split over
Figures 2, 4A:
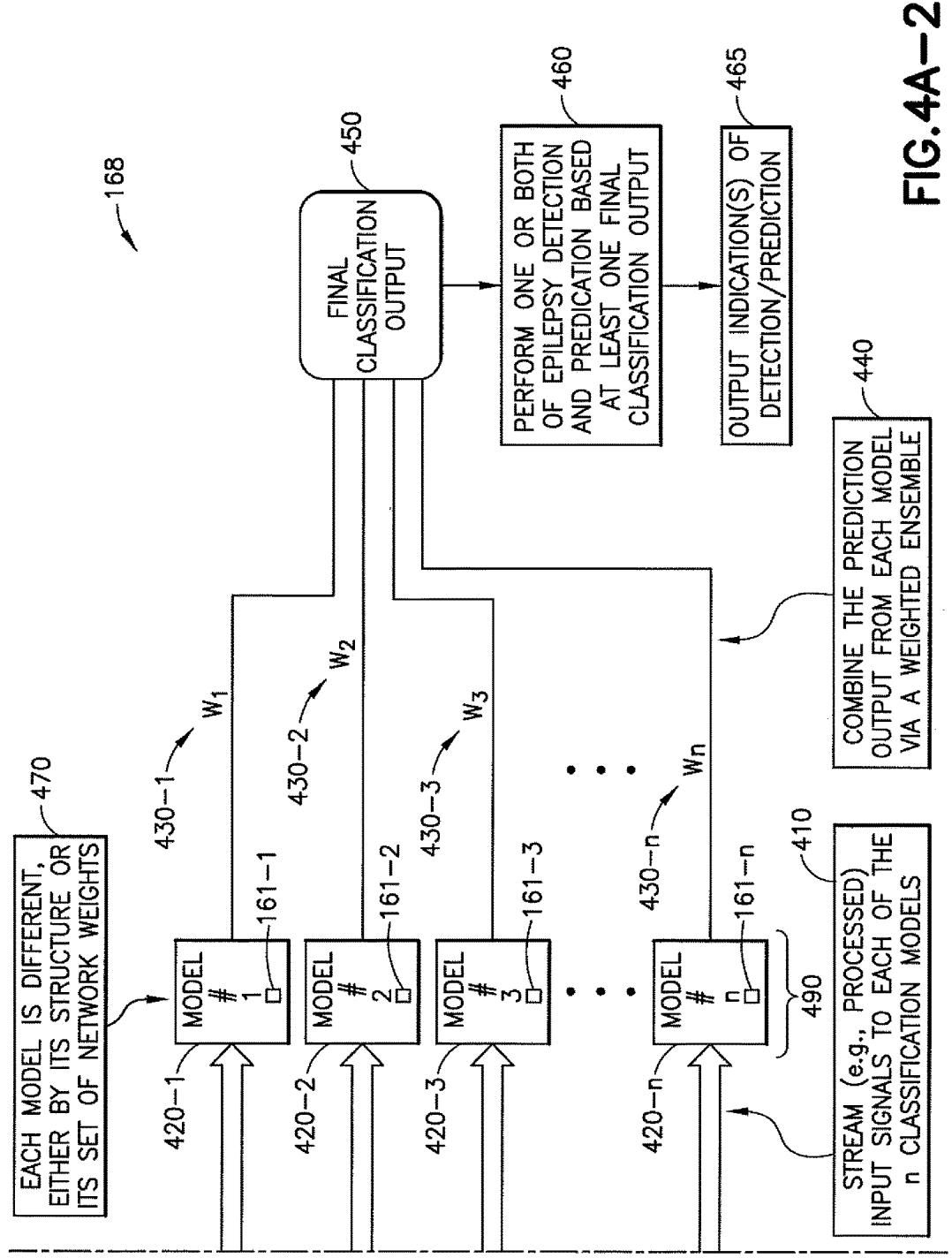
Figure 5:
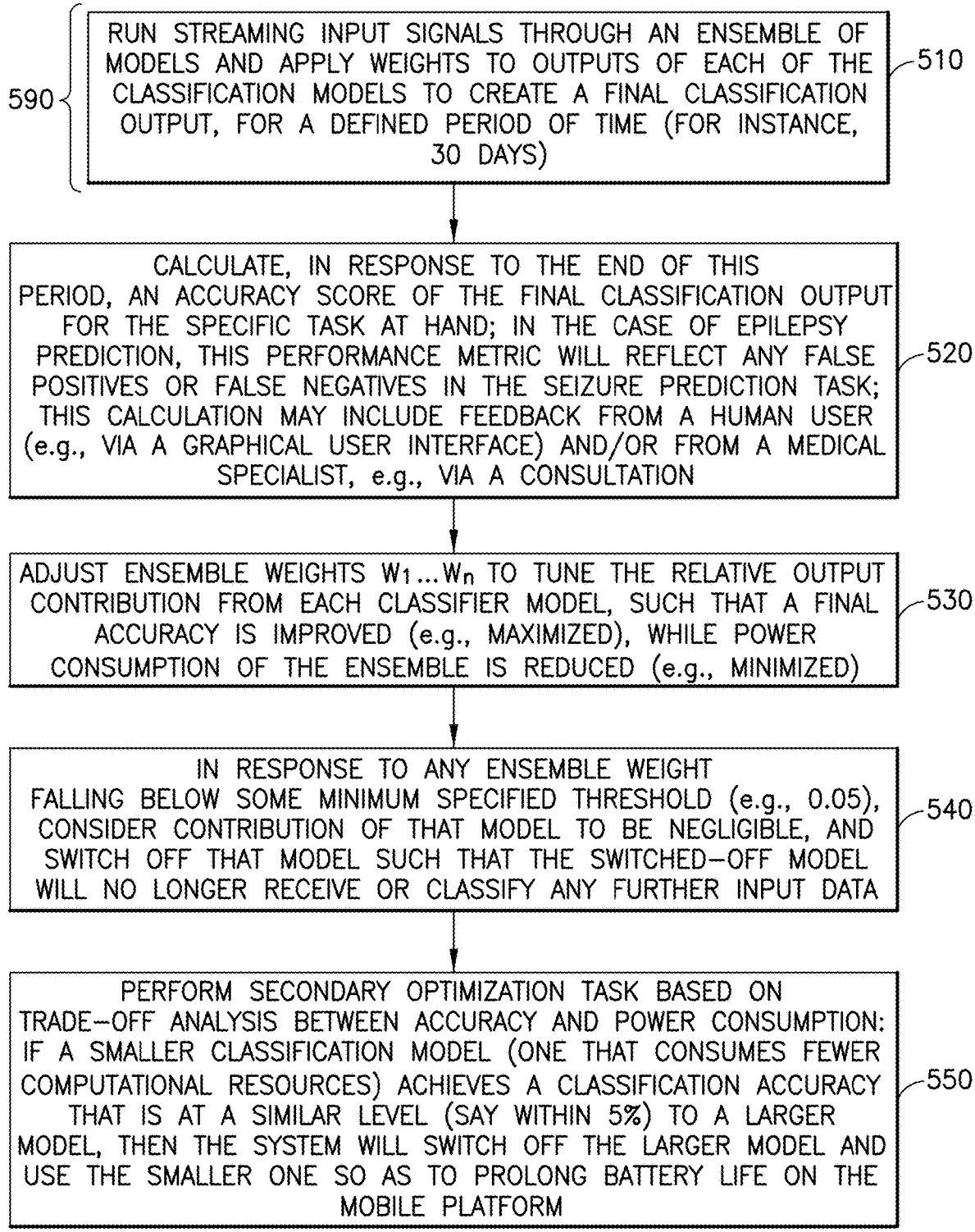
FIG. 5 is a block diagram of a flowchart for performance tuning including model selection in exemplary embodiments.

The ensemble weights 430 are described in more detail in reference, e.g., to FIGS. 4A and 5. Briefly, each weight of the ensemble weights 430 is applied to output of one of the classification models. In this real-time, online system, the ensemble weights 430 can be adjusted as described below.

The user interface circuitry 335 is circuitry that allows a user to interact with the performance-constrained computer platform 300, e.g., via one or more user interfaces, in this case display 386, which may be a touchscreen such as illustrated by display 186 in FIG. 1. Other user interfaces are also possible, in addition to or instead of the display 386, such as keypads and the like.

The network interface(s) 340 are wired or wireless interfaces allowing, e.g., performance-constrained computer platforms 300 and users or others to interact with the performance-constrained computer platform 300 and also allowing the performance-constrained computer platform 300 to interact with the learning-phase computer platform 200. The input signal string interfaces 345 are interfaces for the m sensors 360-1 through 360-$m$, and may include such circuitry as analog-to-digital converters and the like.

The battery system 360 is the power source for the performance-constrained computer platform 300. The computer platform 300 is performance-constrained based on one or both of computing power and battery power. For instance, the wearable computer platform 180 shown in FIG. 1B likely has constraints for both: the computing power of the processor(s) 330 is likely low relative to computing power in a desktop or server computer; and the battery system 360 places a constraint on the platform 180, including how much power the processor(s) 330 can use.

Turning to FIG. 4A, this figure is a block diagram use of a weighted ensemble of classifier models for an inline application of epilepsy seizure detection and prediction in accordance with an exemplary embodiment. This figure may also be considered to be an example of block 168 of FIG. 1B, where the performance-constrained computer platform 300 applies real-time input signal streams through an ensemble of classification models. FIG. 4A is performed by a performance-constrained computer platform 300.

In this example, there are n classifier models 420-1, 420-2, 420-3, . . . , 420-$n$ in an ensemble 490 of models. Each model 420 is assumed to have its own set of network weights 161, labeled as 161-1, 161-2, 161-3, . . . , 161-$n$ to correspond to the models 420-1, 420-2, 420-3, . . . , 420-$n$, respectively. In block 410, the performance-constrained computer platform 300 streams input signals as illustrated by reference 120 to each of the n classification models 420. The EEG traces shown in reference 120 are determined using sensors 360. This streaming may also include processing data from the signals, as previously described in reference to block 130 of FIG. 1A, such that processed data 141 is passed to the ensemble 490 of models.

As block 470 indicates, each model is different, either by its structure or its set of network weights 161. That is, there could be models with the same structure but different sets of network weights 161, or there could be models with different structures (and by definition different network weights). Ensemble weights 430-1, 430-2, 430-3, . . . , and 430-$n$ are shown. Each ensemble weight 430 is applied to an output of one of the n classification models 420. The performance-constrained computer platform 300 in block 440 combines the prediction output from each model via a weighted ensemble. This creates the final classification output 450, which is used for epilepsy seizure detection and prediction. In particular, in block 460, the performance-constrained computer platform 300 performs one or both of epilepsy detection and predication based at least one final classification output. In block 465, the performance-constrained computer platform 300 outputs indication(s) of the detection and/or prediction. This could be performed using the GUI 188, or through other techniques, such as sending a message toward an email address or Internet protocol address or the like, vibrating the performance-constrained computer platform 300, or some combination of these. Note that the block 465 may be performed only in response to detection or prediction of an epileptic seizure, or could be performed whenever the performance-constrained computer platform 300 is turned on and a user is using the display 386/186 (or the display is activated). Thus, block 465 might entail indicating negative events, such as an indication of no detection or no prediction of an epileptic seizure.

Figure 4B:
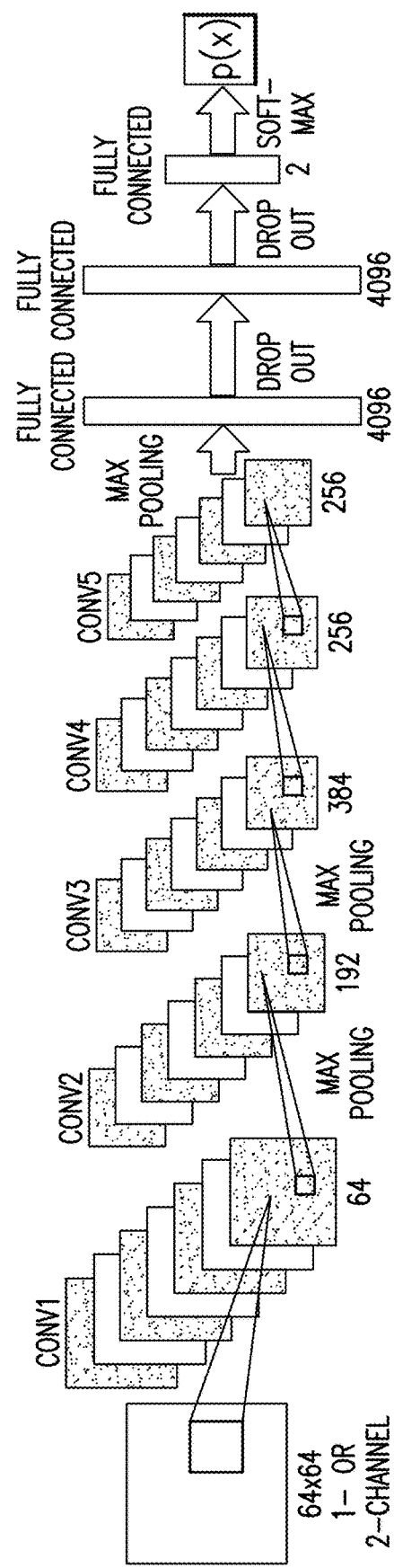
FIG. 4B is an example of a NN classification model used in one of the models of FIG. 4A.

FIG. 4B is an example of a NN classification model used in one of the models of FIG. 4A. This figure shows the structure of a CNN in a way that is standard in the literature. Each box represents a 'feature map', which are units that are responsible for pattern matching in the NN. The lines show how a patch of the input image (or part of a feature map in previous layer) feeds into the subsequent layers. The bars at the right-most part of the image (and labeled with "fully connected") show layers of fully-connected neurons. These are often used in CNNs to enable a multitude of pattern-matching elements to be merged into a single classification output (in this example, p(x)).

Turning to FIG. 5, this figure is a block diagram of a flowchart for performance tuning including model selection in exemplary embodiments. FIG. 5 is performed by a performance-constrained computer platform 300. In block 510, the performance-constrained computer platform 300 runs streaming input signals through an ensemble of models and applies weights to outputs of each of the classification models to create a final classification output, for a defined period of time (for instance, 30 days). As indicated by reference 590, this is part of performing one or both of epilepsy seizure detection and prediction.

The performance-constrained computer platform 300 in block 520 calculates, in response to the end of this period, an accuracy score of the final classification output 450 for the specific task at hand. Such an accuracy score could be reported using a performance metric determined, e.g., via sensitivity, specificity, accuracy, associated confidence interval and ROC (receiver operating characteristic) analysis. In the case of epilepsy prediction, this accuracy score can reflect any false positives or false negatives in the seizure prediction task. This calculation may include feedback from a human user (e.g., via a graphical user interface 188) and/or from a medical specialist, e.g., via a consultation.

In block 530, the performance-constrained computer platform 300 adjusts ensemble weights 430, $w_1 \ldots w_n$, to tune the relative output contribution from each classifier model, such that a final accuracy score is improved (e.g., maximized), while power consumption of the ensemble 490 is reduced (e.g., minimized). This could use techniques of calculus (rate of change of training loss) to determine how to adjust the ensemble weights. This is a standard method in training NNs, and any such techniques can be used. There would be an algorithm implemented in the system to find an optimal (or at least improved) trade-off between classification accuracy (e.g., as measured by the accuracy score) and power consumed by the hardware. The improvement in the accuracy score is relative to the previously determined accuracy score. In these types of systems, the power consumption is typically directly proportional to the computational resources used. So if the system is using fewer resources on the CPU or RAM or both, it may be assumed the system is consuming less power. These levels could be estimated, instead of directly measuring them.

In block 540, the performance-constrained computer platform 300, in response to any ensemble weight 430 falling below some minimum specified threshold (e.g., 0.05), considers contribution of that model to be negligible, and switches off that model 420 such that the switched-off model 420 will no longer receive or classify any further input data. That is, the switched-off model 420 no longer is used when performing one or both of epilepsy seizure detection and prediction.

The performance-constrained computer platform 300 in block 550 may perform a secondary optimization task based on a trade-off analysis between accuracy and power consumption. If a smaller classification model (e.g., one that consumes fewer computational resources relative to larger model), e.g., 420-x achieves a classification accuracy that is at a similar level (say within 5%, five percent) to a larger model (e.g., one that consumes higher computational resources relative to the smaller model), e.g., 420-y, then the system (e.g., performance-constrained computer platform 300) will switch off the larger model 420-y and use the smaller one 420-x so as to prolong battery life on the mobile platform. That is, the switched-off model 420-y no longer is used but the smaller model 420-x is used when performing one or both of epilepsy seizure detection and prediction. Although a metric of an amount of computational resources to distinguish small from large classification models, other metrics might be used, such as numbers of layers of the models.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following abbreviations that may be found in the specification and/or the drawing figures are defined as follows:
2D two dimensional
CNN convolutional neural networks
CPU central processing unit
ECG Electrocardiography or Electrocardiogram
EEG Electroencephalography or Electroencephalogram
EMG Electromyography or Electromyogram
GPU graphics processing unit
GUI graphical user interface
NN neural network
RAM random access memory

What is claimed is:

1. A method, comprising:
    performing one or both of epilepsy seizure detection and prediction at least by performing the following:
        running a plurality of input signals from sensors for epilepsy seizure detection through a plurality of different classification models that have already been trained, that have internal network weights that are not adjustable after training, and that create individual prediction outputs on individual outputs for classifying the plurality of input signals as one or both of an epilepsy seizure detection and an epilepsy seizure prediction; and
        applying weights to the outputs of each of the classification models to create a final classification output;
    adjusting the weights to tune relative output contribution from each classification model in order that accuracy of the final classification output is improved, while power consumption of all the classification models is reduced; and
    performing the one or both of the epilepsy seizure detection and prediction with the adjusted weights.

2. The method of claim 1, wherein the adjusting the weights is performed in response to the performing of the one or both of epilepsy seizure detection and prediction being performed for a defined time period.

3. The method of claim 1, further comprising outputting one or more indications of one or both of an epilepsy seizure detection and an epilepsy seizure prediction.

4. The method of claim 1, further comprising:
    in response to a weight for a classification model falling below a minimum specified threshold, switching off that model such that the switched-off model is no longer used when performing one or both of epilepsy seizure detection and prediction.

5. The method of claim 1, further comprising:
    determining that a first classification model that consumes fewer computational resources relative to a larger model achieves a classification accuracy that is at a similar level to the larger model that consumes higher computational resources relative to the smaller model; and
    switching off the larger classification model while still using the smaller classification model when performing one or both of epilepsy seizure detection and prediction.

6. The method of claim 1, wherein multiple ones of the plurality of classification models are different in their structure.

7. The method of claim 1, wherein the plurality of classification models comprise one or more of neural networks and convolutional neural networks.

8. The method of claim 1, wherein each of the plurality of classification models has a set of network weights, and the set of network weights has been previously determined using input streams from a plurality of input signals from sensors for epilepsy seizure detection, wherein each of the set of network weights is fixed while performing one or both of epilepsy seizure detection and prediction.

9. The method of claim 8, wherein the sets of network weights have been previously determined using input streams from a plurality of different users.

10. An apparatus, comprising:
one or more memories comprising program instructions;
one or more processors, the one or more processors causing, in response to retrieval and execution of the program instructions, operations comprising:
performing one or both of epilepsy seizure detection and prediction at least by performing the following:
running a plurality of input signals from sensors for epilepsy seizure detection through a plurality of different classification models that have already been trained, that have internal network weights that are not adjustable after training, and that create individual prediction outputs on individual outputs for classifying the plurality of input signals as one or both of an epilepsy seizure detection and an epilepsy seizure prediction; and
applying weights to the outputs of each of the classification models to create a final classification output;
adjusting the weights to tune relative output contribution from each classification model in order that accuracy of the final classification output is improved, while power consumption of all the classification models is reduced; and
performing the one or both of the epilepsy seizure detection and prediction with the adjusted weights.

11. The apparatus of claim 10, wherein the adjusting the weights is performed in response to the performing of the one or both of epilepsy seizure detection and prediction being performed for a defined time period.

12. The apparatus of claim 10, wherein the apparatus comprises a display and wherein the one or more processors further cause, in response to retrieval and execution of the program instructions, an additional operation comprising: outputting to the display one or more indications of one or both of an epilepsy seizure detection and an epilepsy seizure prediction.

13. The apparatus of claim 10, wherein the one or more processors further cause, in response to retrieval and execution of the program instructions, an additional operation comprising:
in response to a weight for a classification model falling below a minimum specified threshold, switching off that model such that the switched-off model is no longer used when performing one or both of epilepsy seizure detection and prediction.

14. The apparatus of claim 10, wherein the one or more processors further cause, in response to retrieval and execution of the program instructions, additional operations comprising:

determining that a first classification model that consumes fewer computational resources relative to a larger model achieves a classification accuracy that is at a similar level to the larger model that consumes higher computational resources relative to the smaller model; and
switching off the larger classification model while still using the smaller classification model when performing one or both of epilepsy seizure detection and prediction.

15. The apparatus of claim 10, wherein multiple ones of the plurality of classification models are different their structure, and wherein the plurality of classification models comprise one or more of neural networks or convolutional neural networks.

16. The apparatus of claim 10, wherein each of the plurality of classification models has a set of network weights, and the set of network weights has been previously determined using input streams from a plurality of input signals from sensors for epilepsy seizure detection, wherein each of the set of network weights is fixed while performing one or both of epilepsy seizure detection and prediction.

17. The apparatus of claim 16, wherein the sets of network weights have been previously determined using input streams from a plurality of different users.

18. The apparatus of claim 10, wherein the apparatus is wearable on a human being.

19. The method of claim 1, wherein the plurality of classification models that have already been trained have been previously trained on one or more patients, and where the input signals are from a new patient and the method is performed for the new patient.

20. A computer program product comprising a non-transitory computer readable storage medium having program instructions embodied therewith, the program instructions executable by a computer system to cause the computer system to perform operations comprising:
performing one or both of epilepsy seizure detection and prediction at least by performing the following:
running a plurality of input signals from sensors for epilepsy seizure detection through a plurality of different classification models that have already been trained, that have internal network weights that are not adjustable after training, and that create individual prediction outputs on individual outputs for classifying the plurality of input signals as one or both of an epilepsy seizure detection and an epilepsy seizure prediction; and
applying weights to the outputs of each of the classification models to create a final classification output;
adjusting the weights to tune relative output contribution from each classification model in order that accuracy of the final classification output is improved, while power consumption of all the classification models is reduced; and
performing the one or both of the epilepsy seizure detection and prediction with the adjusted weights.

* * * * *